US009102965B2

(12) United States Patent
Genta et al.

(10) Patent No.: US 9,102,965 B2
(45) Date of Patent: Aug. 11, 2015

(54) SACCHARIDE-SOLUTION PRODUCING APPARATUS, FERMENTATION SYSTEM, SACCHARIDE-SOLUTION PRODUCING METHOD, AND FERMENTATION METHOD

(71) Applicant: MITSUBISHI HEAVY INDUSTRIES MECHATRONICS SYSTEMS, LTD., Kobe-shi, Hyogo (JP)

(72) Inventors: Minoru Genta, Tokyo (JP); Seiichi Terakura, Tokyo (JP); Hideo Suzuki, Tokyo (JP); Gaku Kondo, Tokyo (JP); Michio Nishiyama, Tokyo (JP)

(73) Assignee: MITSUBISHI HEAVY INDUSTRIES MECHATRONICS SYSTEMS, LTD., Kobe-shi (JP)

( * ) Notice: Subject to any disclaimer, the term of this patent is extended or adjusted under 35 U.S.C. 154(b) by 0 days.

(21) Appl. No.: 13/782,545

(22) Filed: Mar. 1, 2013

(65) Prior Publication Data

US 2013/0196424 A1 Aug. 1, 2013

Related U.S. Application Data

(62) Division of application No. 13/578,116, filed as application No. PCT/JP2011/050448 on Jan. 13, 2011.

(51) Int. Cl.
*C12M 1/00* (2006.01)
*C12P 19/14* (2006.01)
(Continued)

(52) U.S. Cl.
CPC ............... *C12P 19/14* (2013.01); *C12M 21/12* (2013.01); *C12M 43/02* (2013.01); *C12M 45/02* (2013.01);
(Continued)

(58) Field of Classification Search
CPC ....... C12M 21/12; C12M 43/02; C12M 45/02
USPC ...................... 435/283.1, 289.1, 290.1, 291.1
See application file for complete search history.

(56) References Cited

U.S. PATENT DOCUMENTS 3,985,728 A * 10/1976 Lin .............................. 536/120
4,152,197 A   5/1979 Lindahl et al.
(Continued)

FOREIGN PATENT DOCUMENTS

CA   2660990 A1   8/2009
CA   2666152 A1   4/2010
(Continued)

OTHER PUBLICATIONS

JP2009-183805 English Machine translation.*
(Continued)

*Primary Examiner* — Nathan Bowers
*Assistant Examiner* — Timothy Barlow
(74) *Attorney, Agent, or Firm* — Westerman, Hattori, Daniels & Adrian, LLP (57) ABSTRACT

A saccharide-solution producing apparatus 11A according to the present invention is a saccharide-solution producing apparatus for producing a saccharide solution 22 derived from a carbohydrate-based material 21, and includes a saccharide-solution controlling unit 15A that controls the saccharide solution derived from the carbohydrate-based material 21, a cellulosic biomass saccharifying unit 16 that saccharifies hydrothermally treated biomass obtained by hydrothermally decomposing a cellulosic biomass material 35 that contains a lignin component and a hemicellulose component, and produces a diluted saccharide solution 37, and a diluted-saccharide-solution supply pipe L11 that mixes the diluted saccharide solution 37 produced by the cellulosic biomass saccharifying unit 16 into the saccharide-solution controlling unit 15A. With this configuration, it is possible to improve production efficiency of the saccharide solution 22 and to realize cost reduction.

10 Claims, 6 Drawing Sheets

(51) Int. Cl.
  *C13K 1/02* (2006.01)
  *C12P 19/02* (2006.01)
  *C12P 7/10* (2006.01)
  *C12M 1/33* (2006.01)

(52) U.S. Cl.
  CPC .............. *C12M 45/09* (2013.01); *C12M 45/20* (2013.01); *C12P 7/10* (2013.01); *C12P 19/02* (2013.01); *C13K 1/02* (2013.01); *C12P 2201/00* (2013.01); *C12P 2203/00* (2013.01); *Y02E 50/16* (2013.01); *Y02T 50/678* (2013.01)

(56) References Cited

U.S. PATENT DOCUMENTS

| | | | |
|---|---|---|---|
| 4,746,401 | A | 5/1988 | Roberts et al. |
| 4,859,322 | A | 8/1989 | Huber |
| 5,348,871 | A | 9/1994 | Scott et al. |
| 5,411,594 | A | 5/1995 | Brelsford |
| 5,424,417 | A | 6/1995 | Torget et al. |
| 5,466,108 | A | 11/1995 | Piroska |
| 6,022,419 | A | 2/2000 | Torget et al. |
| 6,419,788 | B1 | 7/2002 | Wingerson |
| 8,123,864 | B2 | 2/2012 | Christensen et al. |
| 8,163,517 | B2 | 4/2012 | Genta et al. |
| 2005/0250192 | A1 | 11/2005 | Shanmugam et al. |
| 2007/0231869 | A1 | 10/2007 | Holmgren et al. |
| 2007/0259412 | A1 | 11/2007 | Belanger et al. |
| 2008/0020437 | A1 | 1/2008 | Savarese |
| 2008/0032344 | A1 | 2/2008 | Fallavollita |
| 2008/0044891 | A1 | 2/2008 | Kinley et al. |
| 2008/0299628 | A1* | 12/2008 | Hallberg et al. .............. 435/139 |
| 2010/0108567 | A1 | 5/2010 | Medoff |
| 2010/0184176 | A1 | 7/2010 | Ishida et al. |
| 2010/0269990 | A1 | 10/2010 | Dottori et al. |
| 2010/0285574 | A1 | 11/2010 | Genta et al. |
| 2010/0330638 | A1 | 12/2010 | Aita et al. |
| 2011/0079219 | A1 | 4/2011 | McDonald et al. |
| 2011/0314726 | A1 | 12/2011 | Jameel et al. |
| 2012/0006320 | A1 | 1/2012 | Nguyen |
| 2012/0315683 | A1 | 12/2012 | Mosier et al. |
| 2014/0004571 | A1 | 1/2014 | Garrett et al. |
| 2014/0273127 | A1 | 9/2014 | Fuchs et al. |

FOREIGN PATENT DOCUMENTS

| | | | |
|---|---|---|---|
| CA | 2654306 C | | 10/2013 |
| EP | 0 098 490 A2 | | 1/1984 |
| JP | 09-507386 A | | 7/1997 |
| JP | 11-506934 A | | 6/1999 |
| JP | 2002-059118 A | | 2/2002 |
| JP | 2003-311141 A | | 11/2003 |
| JP | 2004-105855 A | | 4/2004 |
| JP | 2005-027541 A | | 2/2005 |
| JP | 2005-168335 A | | 6/2005 |
| JP | 2005-205252 A | | 8/2005 |
| JP | 2005-229821 A | | 9/2005 |
| JP | 2006-136263 A | | 6/2006 |
| JP | 2006-223152 A | | 8/2006 |
| JP | 2006-289164 A | | 10/2006 |
| JP | 2007-202560 A | | 8/2007 |
| JP | 2007-301472 A | | 11/2007 |
| JP | 2008-054608 A | | 3/2008 |
| JP | 2008-104452 A | | 5/2008 |
| JP | 2008-278825 A | | 11/2008 |
| JP | 2009-183153 A | | 8/2009 |
| JP | 2009-183154 A | | 8/2009 |
| JP | 2009-183805 | * | 8/2009 |
| JP | 2009-183805 A | | 8/2009 |
| JP | 2010-17084 A | | 1/2010 |
| JP | 2010-029862 A | | 2/2010 |
| JP | 4427583 B2 | | 3/2010 |
| JP | 4427584 B2 | | 3/2010 |
| JP | 4436429 B1 | | 3/2010 |
| JP | 4764527 B1 | | 9/2011 |
| JP | 4764528 B1 | | 9/2011 |
| JP | 2010-082620 A | | 4/2012 |
| WO | WO84/03304 | * | 8/1984 |
| WO | 96-40970 A1 | | 12/1996 |
| WO | 2008-120662 A1 | | 10/2008 |
| WO | 2009/096060 A1 | | 8/2009 |
| WO | 2009/096062 A1 | | 8/2009 |
| WO | WO 2009/124240 | * | 10/2009 |
| WO | 2010/038302 A1 | | 4/2010 |

OTHER PUBLICATIONS

Written Opinion of ISA PCT/JP/050448, mailing date of Apr. 19, 2011.
Genda Minoru, "NEDO ni yoru Biomass Energy to Ko Koritsu Tenkan Gijutsu Kaihatsu 1) Suinetsu Bunkaiho to Koso Bunkaiho o Kumiawaseta Nogyo Zansa to no Cellulose-kei Biomass no Tei Cost Toka Gijutsu no Kaihatsu", Clean Energy, vol. 19, pp. 11-14.
International Search Report for PCT/JP2011/050448, mailing date of Apr. 19, 2011.
Written Opinion of International Searching Authority PCT/JP2011/050448, mailing date of Apr. 19, 2011, Machine translation only (5 pages).
U.S. Office Action dated Feb. 15, 2013, issued in U.S. Appl. No. 13/578,116.
Canadian Notice of Allowance dated Aug. 22, 2013, issued in Canadian Patent Application No. 2666152.
Canadian Notice of Allowance dated Aug. 22, 2013, issued in Canadian Patent Application No. 2713529.
U.S. Office Action dated Oct. 28, 2013, issued in U.S. Appl. No. 12/443,515.
U.S. Office Action dated Oct. 7, 2013, issued in U.S. Appl. No. 13/700,753.
U.S. Restriction/Election dated Aug. 22, 2013, issued in U.S. Appl. No. 13/700,753.
Canadian Office Action dated Nov. 8, 2013, issued in Canadian Patent Application No. 2,801,383 (2 pages).
Indonesian Notice of Allowance dated Nov. 15, 2013, issued in Indonesian Patent Application No. W-00201002623, w/English translation, (5 pages).
Canadian Notice of Allowance dated Jan. 13, 2014, issued in Canadian Patent Application No. 2,744,522 (1 page).
U.S. Non-Final Office Action dated Dec. 16, 2013, issued in U.S. Appl. No. 13/132,034 (29 pages).
U.S. Non-Final Office Action dated Dec. 17, 2013, issued in U.S. Appl. No. 13/203,929 (23 pages).
U.S. Non-Final Office Action dated Jan. 30, 2014 issued in U.S. Appl. No. 12/438,792 (39 pages).
U.S. Non-Final Office Action dated Jan. 30, 2014, issued in U.S. Appl. No. 13/578,116 (22 pages).
Gregg, D. et al., "Bioconversion of Lignocellulosic Residue to Ethanol: Process Flowsheet Development", Biomass and Bioenergy, 1995, vol. 9, No. 1-5, pp. 287-302, Cited in U.S. Office Action dated Dec. 17, 2013.
U.S. Office Action dated Aug. 19, 2013 issued in U.S. Appl. No. 13/578,116.
Arroyo-Lopez, F.N. et al., "Effects of temperature, pH and sugar concentration on the growth parameters of *Saccharomyces cerevisiae, S. kudriavzevii* and their interspecific hybrid", International Journal of Food Microbiology, vol. 131, pp. 120-127 (2009).
Turton, L.J. et al., "Effect of Glucose Concentration in the Growth Medium Upon Neutral and Acidic Fermentation End-products of *Clostridium bifermentans, Clostridium sporogenes* and *Peptostreptococcus anaerobius*", J. Med. Microbiol., vol. 16, pp. 61-67 (1983).
Dien, B.S. et al., "Fermentation of hexose and pentose sugars using a novel ethanologenic *Escherichia coli* strain", Enzyme and Microbial Technology, vol. 23, pp. 366-371 (1998).
U.S. Final Office Action dated Jul. 3, 2014, issued in U.S. Appl. No. 13/578,116 (17 pages).
U.S. Final Office Action dated Aug. 18, 2014, issued in U.S. Appl. No. 13/132,034 (30 pages).
U.S. Final Office Action dated Jun. 13, 2014, issued in U.S. Appl. No. 12/438,792 (26 pages).

(56) References Cited

OTHER PUBLICATIONS

U.S. Non-Final Office Action dated Aug. 27, 2014, issued in U.S. Appl. No. 13/132,040 (53 pages).
U.S. Final Office Action dated Jul. 22, 2014, issued in U.S. Appl. No. 12/443,515 (13 pages).
Kumagai Satoshi et al. " Fractionation and Saccharification of Cellulose and Hemicellulose in Rice Hull by Hot-Compressed-Water Treatment with Two-Step Heating", Journal of the Japan Institute of Energy, Dec. 1, 2003, vol. 83, pp. 776-781, Cited in Notice of Acceptance dated Mar. 4, 2014, issued in Japanese Patent Application No. 2009-252201.
Australian Notice of Acceptance dated Mar. 17, 2014, issued in Australian patent application No. 2011355013 (corresponding to U.S. Appl. No. 13/578,116) (2 pages).
US Final Office Action dated Feb. 13, 2014, issued in U.S. Appl. No. 12/865,273.
Liu, Chaogang, et al., "Continuous Fermentation of Hemicellulose Sugars and Cellulose to Ethanol", International Symposia on Alcohol Fuels, 2005, pp. 1-28, cited in US Final Office Action dated Feb. 13, 2014, issued in U.S. Appl. No. 12/865,273.
Decision of a Patent Grant dated Mar. 4, 2014, issued in JP2009-252201 (corresponding to U.S. Appl. No. 12/443,515, w/English translation) (4 pages).
Decision of a Patent Grant dated Mar. 4, 2014, issued in JP2009-245963 (corresponding to U.S. Appl. No. 12/438,792 , w/English translation) (4 pages).
U.S. Office Action dated Apr. 14, 2014, issued in U.S. Appl. No. 12/443,515 (16 pages).
Canadian Office Action dated Mar. 31, 2014, issued in Canadian Patent Application No. 2,750,753 (3 pages) (corresponding to U.S. Appl. No. 13/203,929).
U.S. Final Office Action dated May 22, 2014, issued in U.S. Appl. No. 13/700,753 (40 pages).
U.S. Final Office Action dated Jun. 3, 2014, issued in U.S. Appl. No. 13/203,929 (22 pages).
Indonesian Office Action dated Nov. 7, 2014, issued in IDW-00200902414, w/English translation (corresponds to U.S. Appl. No. 12/438,792) (6 pages).
Indonesian Office Action dated Nov. 14, 2014, issued in IDW-00201102352, w/English translation (corresponds to U.S. Appl. No. 13/121,969) (7 pages).
Japanes Office Action dated Oct. 14, 2014, issued in Japanese Patent Application No. 2010-154233 (corresponds to U.S. Appl. No. 13/700,753, with English Translation (7 pages).
U.S. Office Action dated Dec. 5, 2014, issued in U.S. Appl. No. 13/121,929.
Canadian Notice of Allowance dated Dec. 5, 2014, issued in Canadian Patent Application No. 2750754 (corresponds to U.S. Appl. No. 13/203,929.
Indonesian Office Action dated Oct. 29, 2014, issued in Indonesian Patent Application No. W00201103522 (corresponds to U.S. Appl. No. 13/203, 929), w/ English translation.

Genta, M. et al., "Suinetsu Bunkaiho to Koso Bunkaiho o Kumiawaseta Nogyo Zansa To no Cellulose Biomass no Tei Cost Toka Gijutsu no Kaihatsu", Heisei 21 Nendo Biomass Energy Kanren Jigyo Seika Hokokukai, Feb. 11, 2010, pp. 55-69, URL, http://www.nedo.go.jp/events/report/FF__00003.html, Cited in JP Office Action dated Oct. 14, 2014.
Lehrburger, E. "Developing biorefineries to produce energy, ethanol and other industrial products", PureVision Technology, Inc., Alternative Energy Conference, Mar. 3, 2005, pp. 1-26, Cited in U.S. Office Action dated Nov. 6, 2014.
U.S. Office Action dated Nov. 6, 2014, issued in U.S. Appl. No. 12/865,273 (27 pages).
Japanese Office Action dated Oct. 14, 2014, issued in Japanese Patent Application No. 2010-154233(corresponds to U.S. Appl. No. 13/700,753), with English Translation (7 pages).
U.S. Office Action dated Dec. 5, 2014, issued in U.S. Appl. No. 13/121,969.
Canadian Notice of Allowance dated Dec. 5, 2014, issued in Canadian Patent Application No. 2750754 (corresponds to U.S. Appl. No. 13/203,848).
Indonesian Office Action dated Oct. 29, 2014, issued in Indonesian Patent Application No. W00201103522 (corresponds to U.S. Appl. No. 13/203,929), w/English translation.
U.S. Notice of Allowance dated Nov. 5, 2014, issued in U.S. Appl. No. 12/443,515.
U.S. Office Action dated Dec. 26, 2014, issued in related U.S. Appl. No. 13/132,040.
International Search Report dated Jul. 3, 2012 issued in International Application No. PCT/JP2012/058460 (corresponds to U.S. Appl. No. 14/381,511).
Written Opinion of the International Searching Authority dated Jul. 3, 2012 issued in International Application No. PCT/JP2012/058460 (corresponds to U.S. Appl. No. 14/381,511).
Decision of a Patent Grant dated Nov. 12, 2013, issued in Japanese Patent Application No. 2013-536355, w/ English translation (corresponds to U.S. Appl. No. 14/381,511) (4 pages).
U.S. Office Action dated Apr. 24, 2015, issued in U.S. Appl. No. 14/381,511 (20 pages).
U.S. Office Action dated Mar. 19, 2015, issued in U.S. Appl. No. 13/121,969 (21 pages).
U.S. Office Action dated Mar. 13, 2015, issued in U.S. Appl. No. 13/722,385 (41 pages).
Notice of Allowance and Fee(s) Due dated Apr. 2, 2015, issued in U.S. Appl. No. 13/132,040 (17 pages).
U.S. Office Action dated Mar. 31, 2015, issued in U.S. Appl. No. 12/865,273 (25 pages).
U.S. Office Action dated May 13, 2015, issued in U.S. Appl. No. 12/438,792 (11 pages).
Non-Final Office Action dated Jun. 19, 2015, issued in U.S. Appl. No. 13/700,753 (34 pages).

* cited by examiner

SACCHARIDE-SOLUTION PRODUCING APPARATUS, FERMENTATION SYSTEM, SACCHARIDE-SOLUTION PRODUCING METHOD, AND FERMENTATION METHOD

CROSS-REFERENCE TO RELATED APPLICATIONS

This application is a Divisional of U.S. application Ser. No. 13/578,116 filed Aug. 9, 2012, and wherein application Ser. No. 13/578,116 is a national stage application filed under 35 USC §371 of International Application No. PCT/JP2011/050448, filed Jan. 13, 2011, the entire contents of which are incorporated herein by reference.

FIELD

The present invention relates to a saccharide-solution producing apparatus, a fermentation system, a saccharide-solution producing method, and a fermentation method for producing a saccharide solution derived from a carbohydrate-based material, and more particularly to improvement in saccharide-solution production efficiency when a saccharide solution is produced from a carbohydrate-based material.

BACKGROUND

Biomass that is organic resources of biological origin is produced by living organisms from water and carbon dioxide by the use of solar energy, and is sustainable and renewable resources. In recent years, as a part of global warming countermeasures, attempts have been extensively made to produce ethanol from biomass that contains a cellulosic material such as woody biomass or herbaceous biomass, and to use the ethanol as various types of fuel or chemical materials. Biomass ethanol produced from the biomass is a renewable natural energy, and the amount of carbon dioxide released into the condition does not increase even if the biomass ethanol is burned. From these perspectives, biomass is attracting attention as available and effective resources and is expected to be used as future energy sources.

The biomass is a collection of living organisms incorporated into the material circulation system in the earth's biosphere or a collection of organic matters derived from the living organisms (see JIS K 3600 1258). For example, the biomass is classified into a forest/woodland type (lumber scraps, lumber from thinning, paper waste and the like), an agricultural type (rice straw, wheat straw, sugarcane residues, rice bran, palm shell, plants and the like), an animal type (domestic animal waste and the like), a fishery type (fish processing residues and the like), and a waste type (left-over food products, garden plants, construction waste, sewerage sludge and the like).

Conventionally, as an ethanol producing method, there is used an ethanol producing method that includes saccharifying biomass or the like that contains a carbohydrate-based material, a cellulosic material or the like to produce a saccharide solution, and fermenting the obtained saccharide solution, thereby producing ethanol. For example, as an ethanol producing method using biomass, the following methods are proposed: an ethanol producing method that includes hydrolyzing collected biomass into saccharides by the addition of sulfuric acid, performing thereafter solid-liquid separation, neutralizing a liquid phase, subjecting the neutralized liquid phase to ethanol fermentation using microorganism such as yeast, and converting the liquid phase into ethanol (see Patent Literatures 1 and 2); and an ethanol producing method that includes performing hydrothermal decomposition by causing collected biomass and pressurized hot water to contact each other in a consolidated condition, thereby obtaining hydrothermally treated biomass, adding enzyme to the obtained hydrothermally treated biomass and saccharifying the obtained hydrothermally treated biomass, thereby obtaining a saccharide solution, and fermenting the obtained saccharide solution, thereby producing ethanol (see Patent Literatures 3 and 4).

CITATION LIST

Patent Literatures

Patent Literature 1: Japanese Patent Application National Publication No. H9-507386
Patent Literature 2: Japanese Patent Application National Publication No. H11-506934
Patent Literature 3: Japanese Patent Application Laid-open No. 2010-29862
Patent Literature 4: Japanese Patent Application Laid-open No. 2010-82620

SUMMARY

Technical Problem

In this case, it is required to ensure a high saccharide recovery ratio and to increase the saccharide concentration of the produced saccharide solution when enzyme is added to the hydrothermally treated biomass obtained from the biomass, in order to saccharify the hydrothermally treated biomass by the method of hydrothermally decomposing the biomass using the pressurized hot water as described in Patent Literatures 3 and 4. Therefore, it is necessary to increase the concentration of the hydrothermally treated biomass that serves as a material when saccharifying the hydrothermally treated biomass by the addition of the enzyme so as to produce the saccharide solution having a high saccharide concentration.

However, when the concentration of the hydrothermally treated biomass increases, there is a problem that the saccharide recovery ratio falls for such a reason as a worse mixed state between the hydrothermally treated biomass and the enzyme.

Furthermore, when the concentration of the hydrothermally treated biomass is high, the power requirement to agitate the hydrothermally treated biomass becomes high in an enzymatic saccharification tank that contains the hydrothermally treated biomass. As a result, there is a problem that power consumption necessary to produce the saccharide solution from the hydrothermally treated biomass increases.

Further, a method of excessively adding enzyme to hydrothermally treated biomass is considered so as to improve the saccharide recovery ratio in a state where the concentration of the hydrothermally treated biomass is high. However, the unit price of the enzyme used to saccharify the hydrothermally treated biomass is high. As a result, when the additive amount of the enzyme by which the enzyme is added to the hydrothermally treated biomass increases, there is a problem that the cost required to produce ethanol rises.

Generally, therefore, a concentration operation such as evaporation concentration is performed so as to obtain a predetermined concentration suited for fermentation for causing, for example, alcohol fermentation after saccharifying the hydrothermally treated biomass.

On the other hand, when various organic materials are produced from a saccharide solution derived from the carbohydrate-based material (obtained by saccharification, extraction, or squeezing), an alcohol fermentation system including a saccharide-solution producing apparatus, for example, is put in a higher alcohol concentration condition as fermentation proceeds and microorganism that cause fermentation become extinct when the concentration of the saccharide solution used for the fermentation is high. Therefore, it is necessary to dilute the saccharide solution (at the saccharide concentration of about 20% to 60%) with water and to control the saccharide concentration.

Therefore, under these circumstances, there has been a demand for an efficient system capable of solving the problems that occur when saccharides are produced by the biomass treatment mentioned above and when various organic materials are produced from the saccharide solution derived from the carbohydrate-based material.

In view of the above problems, an object of the present invention is to provide a saccharide-solution producing apparatus, a fermentation system, a saccharide-solution producing method, and a fermentation method capable of improving saccharide-solution production efficiency and realizing cost reduction.

Solution to Problem

According to an aspect of the present invention, a saccharide-solution producing apparatus for producing a saccharide solution derived from a carbohydrate-based material includes: a saccharide-solution controlling unit that controls the saccharide concentration derived from the carbohydrate-based material; a cellulosic biomass saccharifying unit that saccharifies hydrothermally treated biomass obtained by hydrothermally decomposing a cellulosic biomass material containing a lignin component and a hemicellulose component to produce a diluted saccharide solution; and a diluted-saccharide-solution supply pipe that mixes a diluted saccharide solution produced by the cellulosic biomass saccharifying unit into the saccharide-solution controlling unit.

Advantageously, in the saccharide-solution producing apparatus, the saccharide solution is obtained by saccharifying the carbohydrate-based material or is discharged or squeezed from the carbohydrate-based material.

Advantageously, in the saccharide-solution producing apparatus, the cellulosic biomass saccharifying unit includes a hydrothermal decomposition device that hydrothermally treats the cellulosic biomass material and to produce hydrothermally treated biomass, and a second enzymatic saccharification tank that adds enzyme to the hydrothermally treated biomass to saccharify the hydrothermally treated biomass, and generates the diluted saccharide solution.

Advantageously, in the saccharide-solution producing apparatus, the hydrothermal decomposition device hydrothermally decomposes the cellulosic biomass material while causing the cellulosic biomass material to contact pressurized hot water, transfers a lignin component and a hemicellulose component into the pressurized hot water, and separates the lignin component and the hemicellulose component from the cellulosic biomass material, and a hydrothermally discharged fraction that contains the lignin component and the hemicellulose component and a solid residual fraction that contains a cellulose component are produced as the hydrothermally treated biomass.

Advantageously, in the saccharide-solution producing apparatus, the second enzymatic saccharification tank produces one of or both of a diluted saccharide solution that contains hexose by adding enzyme to the solid residual fraction discharged from the hydrothermal decomposition device and enzymatically decomposing a cellulose component contained in the solid residual fraction, and a diluted saccharide solution that contains pentose by adding enzyme to the hydrothermally discharged fraction discharged from the hydrothermal decomposition device and enzymatically decomposing a hemicellulose component contained in the hydrothermally discharged fraction.

Advantageously, in the saccharide-solution producing apparatus, a saccharide concentration of the diluted saccharide solution is equal to or higher than 0.1 mass % and equal to or lower than 15 mass %.

According to another aspect of the present invention, a fermentation system includes: the saccharide-solution producing apparatus according to any one of aboves; and an alcohol fermentation tank that ferments the saccharide solution to produce an organic material.

According to still another aspect of the present invention, a saccharide-solution producing method for producing a saccharide solution derived from a carbohydrate-based material includes: producing hydrothermally treated biomass by hydrothermally decomposing a cellulosic biomass material containing a lignin component and a hemicellulose component, saccharifying the hydrothermally treated biomass by adding enzyme to the obtained hydrothermally treated biomass to produce a diluted saccharide solution; and producing the saccharide solution derived from the carbohydrate-based material by using the diluted saccharide solution when the saccharide solution is controlled.

Advantageously, in the saccharide-solution producing method, as the saccharide solution, a saccharide solution obtained by saccharifying the carbohydrate-based material or a saccharide solution discharged or squeezed from the carbohydrate-based material is used.

Advantageously, in the saccharide-solution producing method includes: hydrothermally decomposing the cellulosic biomass material while causing the cellulosic biomass material to contact pressurized hot water; transferring a lignin component and a hemicellulose component into the pressurized hot water; separating the lignin component and the hemicellulose component from the cellulosic biomass material; and producing a hydrothermally discharged fraction that contains the lignin component and the hemicellulose component, and a solid residual fraction that contains a biomass solid content. One of or both of the hydrothermally discharged fraction and the solid residual fraction is used as the hydrothermally treated biomass.

Advantageously, in the saccharide-solution producing method, one of or both of a diluted saccharide solution that contains hexose and that is obtained by adding enzyme to the solid residual fraction and by enzymatically decomposing a cellulose component contained in the solid residual fraction, and a diluted saccharide solution that contains pentose and that is obtained by adding enzyme to the hydrothermally discharged fraction and by enzymatically decomposing the hemicellulose component contained in the hydrothermally discharged fraction is used as the diluted saccharide solution.

Advantageously, in the saccharide-solution producing method, a saccharide concentration of the diluted saccharide solution is set equal to or higher than 0.1 mass % and equal to or lower than 15 mass %.

According to still another aspect of the present invention, a fermentation method comprising any one of the saccharide-solution producing methods described above. A saccharide solution obtained by using the saccharide-solution producing method is fermented to produce an organic material.

In addition, to solve the above problems, the following configurations can be employed.

(1) That is, the saccharide-solution producing apparatus can be configured such that, when the saccharide solution is obtained by saccharifying the carbohydrate-based material, the saccharide-solution controlling unit includes a storage tank that stores therein the carbohydrate-based material, and a first enzymatic saccharification tank for enzymatically saccharifying the carbohydrate-based material.

(2) The saccharide-solution producing apparatus can be configured such that, when the saccharide solution is discharged or squeezed from the carbohydrate-based material, the saccharide-solution controlling unit includes a storage tank that stores therein the carbohydrate-based material, and a saccharide-concentration controlling tank.

(3) The saccharide-solution producing method can include adding the saccharide solution to one of or both of a storage tank that stores therein the carbohydrate-based material and a first enzymatic saccharification tank for enzymatically saccharifying the carbohydrate-based material when the saccharide solution is obtained by saccharifying the carbohydrate-based material.

(4) The saccharide-solution producing method can include adding the saccharide solution to one of or both of a storage tank that stores therein the carbohydrate-based material and a saccharide-concentration controlling tank when the saccharide solution is discharged or squeezed from the carbohydrate-based material.

Advantageous Effects of Invention

According to the present invention, saccharide-solution production efficiency can be improved and cost reduction can be realized.

DESCRIPTION OF EMBODIMENTS

Exemplary embodiments of the present invention will be explained below in detail with reference to the accompanying drawings. The present invention is not limited to the contents of the embodiments described below. In addition, constituent elements described below include elements that can be easily assumed by persons skilled in the art, elements that are substantially identical, and so-called equivalents. Furthermore, it is possible to carry out appropriate combinations of the constituent elements described below.

First Embodiment

Figure 1:
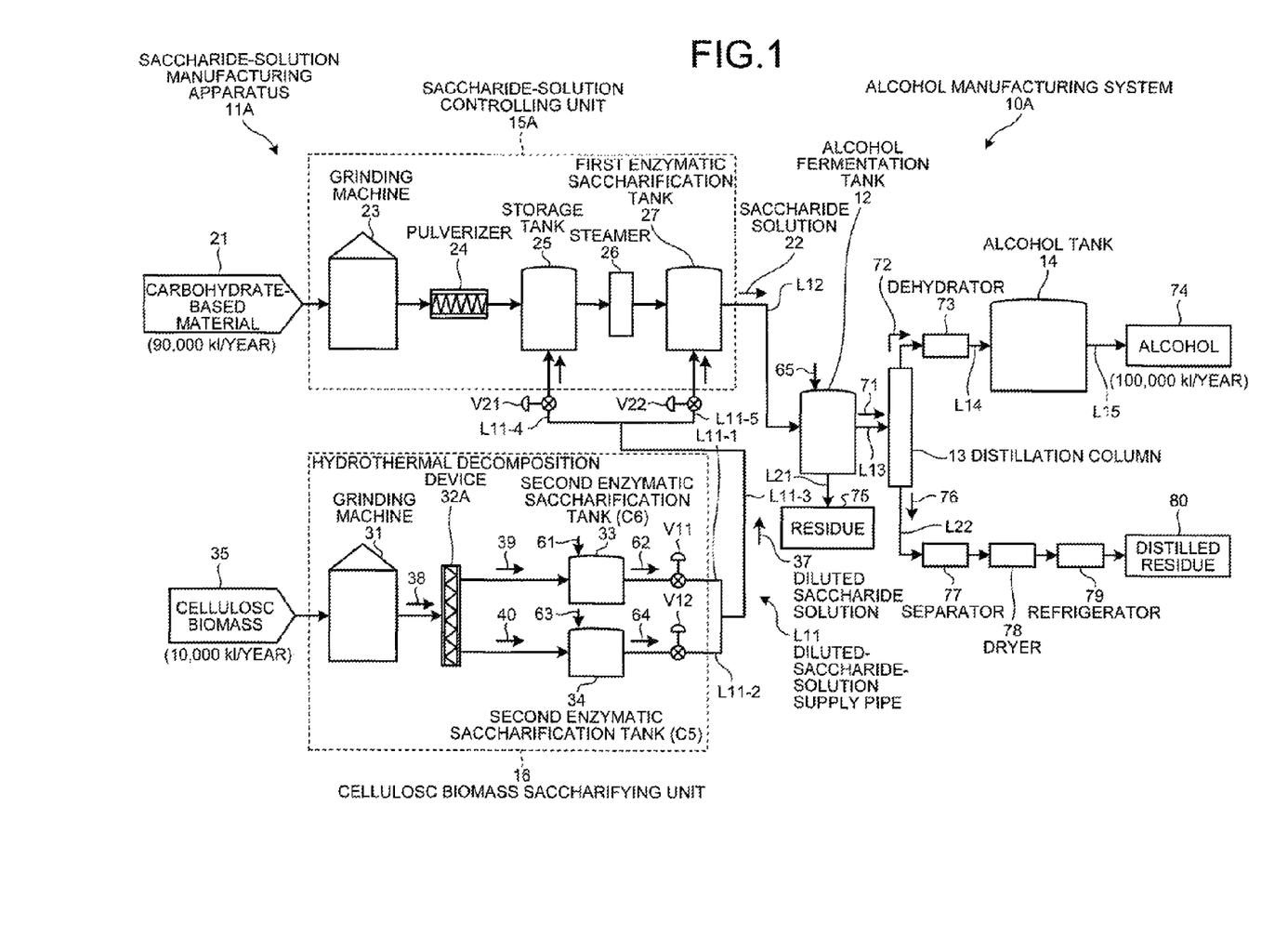
FIG. 1 is a schematic diagram of an alcohol producing system including a saccharide-solution producing apparatus according to a first embodiment of the present invention.

A saccharide-solution producing apparatus according to a first embodiment of the present invention is described with reference to the drawings. FIG. 1 is a schematic diagram of an alcohol producing system including the saccharide-solution producing apparatus according to the first embodiment of the present invention. As shown in FIG. 1, an alcohol producing system 10A includes a saccharide-solution producing apparatus 11A according to the present embodiment, an alcohol fermentation tank 12, a distillation column 13, and an alcohol tank 14.

The saccharide-solution producing apparatus 11A according to the present embodiment includes a saccharide-solution controlling unit 15A and a cellulosic biomass saccharifying unit 16.

(Saccharide-Solution Controlling Unit)

The saccharide-solution controlling unit 15A produces a saccharide solution 22 from a carbohydrate-based material 21. The saccharide-solution controlling unit 15A includes a grinding machine 23, a pulverizer 24, a storage tank 25, a cooker 26, and a first enzymatic saccharification tank 27. The carbohydrate-based material 21 is ground by the grinding machine 23 and further pulverized by the pulverizer 24. The pulverized carbohydrate-based material 21 is stored in the storage tank 25. After the cooker 26 steams the carbohydrate-based material 21 stored in the storage tank 25, a saccharide concentration of the carbohydrate-based material 21 stored in the storage tank 25 is controlled and the carbohydrate-based material 21 is saccharified in the first enzymatic saccharification tank 27. In the present embodiment, a diluted saccharide solution 37, to be described later, is added into one of or both of the storage tank 25 and the first enzymatic saccharification tank 27, and is used as a diluted solution when the saccharide solution 22 is produced from the carbohydrate-based material 21. As described later, by adding the diluted saccharide solution 37 into the storage tank 25, the carbohydrate-based material 21 is diluted with the diluted saccharide solution 37. The carbohydrate-based material 21 within the storage tank 25 can be thereby easily enzymatically saccharified in the first enzymatic saccharification tank 27 and can be easily transferred.

(Cellulosic Biomass Saccharifying Unit)

The cellulosic biomass saccharifying unit 16 includes a grinding machine 31, a hydrothermal decomposition device 32A, a second enzymatic saccharification tank including a enzymatic saccharification tank (C6) 33, and a second enzymatic saccharification tank (C5) 34. The cellulosic biomass saccharifying unit 16 saccharifies hydrothermally treated biomass that is obtained by hydrothermally decomposing a cellulosic biomass material 35, and produces the diluted saccharide solution 37.

The biomass is not limited to a specific type but signifies a collection of living organisms incorporated into the material circulation system in the earth's biosphere or a collection of organic matters derived from the living organisms (see JIS K 3600 1258). As the biomass, for example, it is preferable to use, particularly woody biomass, broadleaf trees, ligno-cellulose resources as herbaceous biomass, agricultural waste, left-over food products or the like. In the present embodiment, for example, the cellulosic biomass material 35 is rice straw, wheat straw, corn stover (corn stalks), corncobs (corn cobs), or EFB (empty fruit bunch of oil palms). However, the present embodiment is not limited thereto.

The cellulosic biomass material 35 is ground into a ground biomass material 38 of 5 millimeters or less, for example, by the grinding machine 31. The ground biomass material 38 is hydrothermally treated by the hydrothermal decomposition device 32A. The hydrothermal decomposition device 32A hydrothermally decomposes the ground biomass material 38 while causing the ground biomass material 38 and pressurized hot water countercurrently contact with each other, transfers lignin components and hemicellulose components into the pressurized hot water, and separates the lignin components and the hemicellulose components from a biomass solid content. The hydrothermally treated biomass is obtained by hydrothermally treating the ground biomass material 38 in the hydrothermal decomposition device 32A, and is separated into a solid residual fraction 39 that is the biomass solid content and a hydrothermally treated fraction 40 that is the lignin components and the hemicellulose components transferred into the pressurized hot water.

Figure 2:
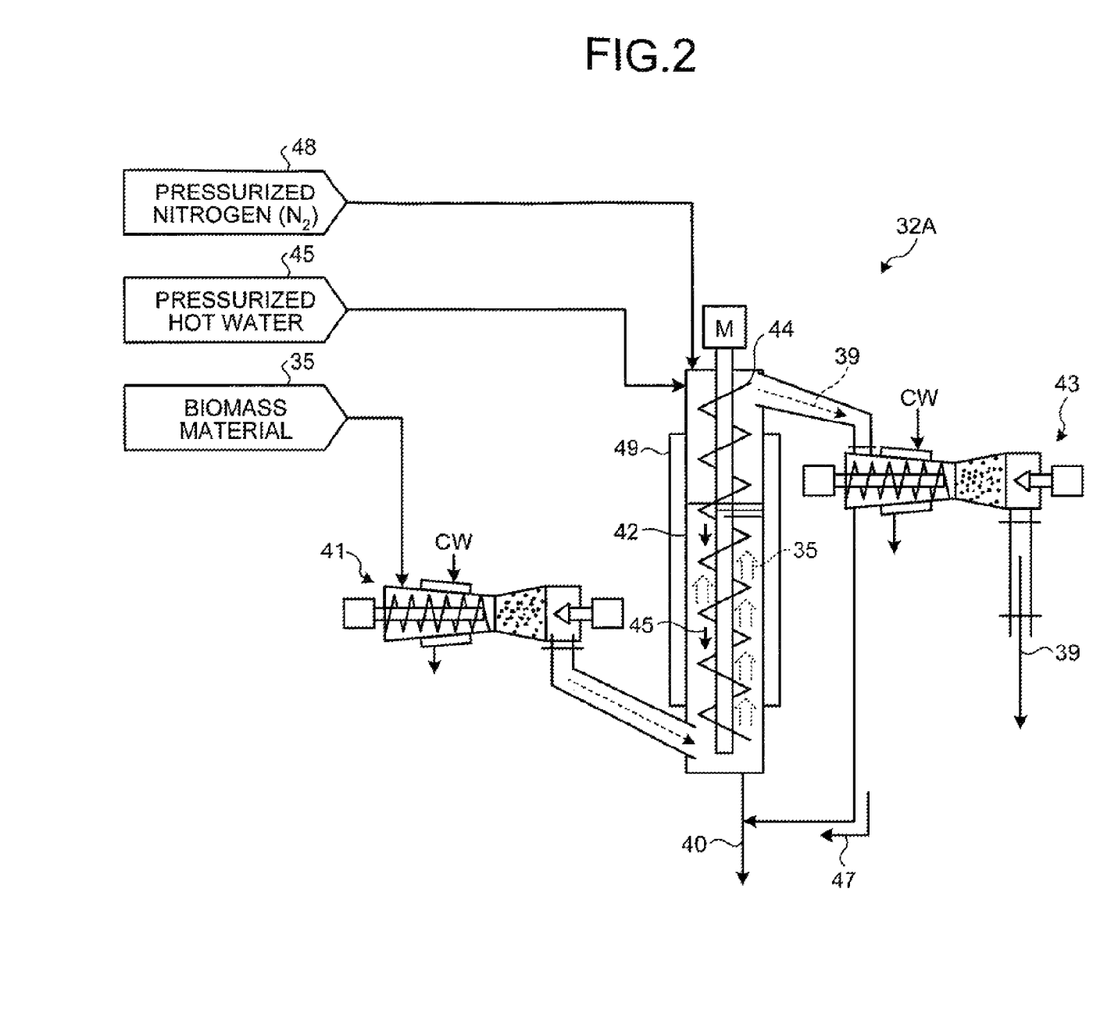
FIG. 2 depicts a configuration of a hydrothermal decomposition device.

FIG. 2 depicts a configuration of the hydrothermal decomposition device 32A. As shown in FIG. 2, the hydrothermal decomposition device 32A includes a biomass supply device 41, a reaction device 42, and a biomass discharge device 43. The biomass supply device 41 supplies the cellulosic biomass material (hereinafter, "biomass material") 35 from under an normal pressure to under an increased pressure.

The reaction device 42 transports the supplied biomass material 35 from one side (a lower side in the present embodiment) to the other side (an upper side) within a device main body by a screw unit 44, supplies pressurized hot water 45 into the device main body from the other side (the upper side) different from a portion from which the biomass material 35 is supplied, and hydrothermally decomposes the biomass material 35 while causing the biomass material 35 and the pressurized hot water 45 to countercurrently contact with each other. With this configuration, the lignin components and the hemicellulose components are transferred into the pressurized hot water 45, separated from within the biomass material 35, and discharged from the reaction device 42 as the hydrothermally discharged fraction 40.

The biomass discharge device 43 extracts the solid residual fraction 39 that is the biomass solid content from the other side of the reaction device 42. In FIG. 2, reference sign 47 denotes a dehydration liquid, 48 denotes pressurized nitrogen (N2), and 49 denotes a temperature jacket.

In the present embodiment, the biomass material 35 is supplied from a lower end side. However, the present embodiment is not limited thereto. The biomass material 35 can be alternatively and conversely supplied from an upper end side, in which case, the pressurized hot water 45 is supplied from the lower end side.

Examples of the biomass supply device 41 that supplies the biomass material 35 from under a normal pressure to under an increased pressure include units such as a screw feeder, a piston pump, and a slurry pump.

While the reaction device 42 is a vertical device in the present embodiment, the present embodiment is not limited thereto. Alternatively, an inclined reaction device or a horizontal reaction device can be used as the reaction device 42. In this case, the reason for using the vertical or inclined type is that the vertical or inclined reaction device can promptly discharge gas generated in a hydrothermal decomposition reaction, gas brought into a material or the like from above, and is preferably used.

In the present embodiment, before biomass is supplied, the biomass is pretreated by the use of the grinding machine 31 that serves as a pretreatment device. However, the present invention is not limited thereto, and when a particle diameter of the biomass material 35 is sufficiently small, there is no need to provide the grinding machine 31. Alternatively, a wet scrubber can wash the biomass material 35. It is assumed that the biomass material 35 can be supplied directly to the reaction device 42 without pulverizing the biomass material 35 when the biomass material 35 is rice hulls, for example.

A reaction temperature in the reaction device 42 is preferably set to be equal to or higher than 180° C. and equal to or lower than 240° C., more preferably set to be equal to or higher than 200° C. and equal to or lower than 230° C. for the following reasons. That is, at a low temperature below 180° C., if the hydrothermal decomposition rate is low, a long decomposition time becomes necessary, and the size of the device has to be large. Therefore, the low temperature below 180° C. is not preferable. On the other hand, a temperature higher than 240° C. excessively increases the decomposition rate, increases transfer of cellulose components from a solid side to a liquid side, and promotes excessively decomposing hemicellulosic saccharides. Therefore, the temperature higher than 240° C. is not preferable. Furthermore, the hemicellulose components are dissolved at about 140° C. or higher, the cellulose components are dissolved at about 230° C. or higher, and the lignin components are dissolved at about 140° C. or higher. Therefore, the reaction temperature is preferably set within a range from 180° C. to 240° C. within which the hemicellulose components and the lignin components are decomposed at a sufficient decomposition rate.

The reaction pressure of the hydrothermal decomposition is preferably set to a pressure higher by 0.1 MPa to 0.5 MPa than the saturated vapor pressure of water at each temperature, which allows the pressurized hot water to stay inside the device.

The reaction time is preferably set to be equal to or shorter than 20 minutes, more preferably set to be equal to or higher than 3 minutes and equal to or lower than 10 minutes. This is because the ratio of an excessively decomposed material increases at a reaction time that is too long and it is not preferable.

In the present embodiment, it is preferable that flow of the pressurized hot water 45 and that of the biomass material 35 within the main body of the reaction device 42 are so-called counter flows for causing the biomass material 35 and the pressurized hot water 45 to countercurrently contact each other so that the biomass material 35 and the pressurized hot water 45 can contact each other, can be agitated, and can flow.

In the reaction device 42, the solid content of the biomass material 35 is supplied from a bottom side, the pressurized hot water 45 is supplied from a top side, and the biomass material 35 and the pressurized hot water 45 contact each other and move, whereby the pressurized hot water (hot water, a liquid into which the decomposed material is dissolved) 45 moves while soaking between solid particles in a counter flow to the flow of the biomass material 35 that is the solid content.

In the present embodiment, the pressurized nitrogen (N2) 48 is supplied into the reaction device 42 because a gaseous part is present within the reaction device 42. However, the present invention is not limited thereto and the pressurized N2 48 is not necessarily supplied into the reaction device 42.

It is possible to increase the temperature of the biomass material 35 in the reaction device 42 by allowing the biomass material 35 to contact the pressurized hot water 45 and to directly exchange heat with the pressurized hot water 45 in the reaction device 42. The biomass material 35 can be heated from outside by using steam or the like as needed.

In the present embodiment, by causing the biomass material 35 and the pressurized hot water 45 to countercurrently contact each other, components easily soluble into the pressurized hot water 45 are sequentially discharged, and a temperature gradient occurs from an input part from which the biomass material 35 is input to a hot-water input part. This can suppress the hemicellulose components from being excessively decomposed and can eventually efficiently recover pentose components. Furthermore, by causing the biomass material 35 and the pressurized hot water 45 to countercurrently contact each other, heat recovery can be made, which is preferable in view of system efficiency.

Figure 3:
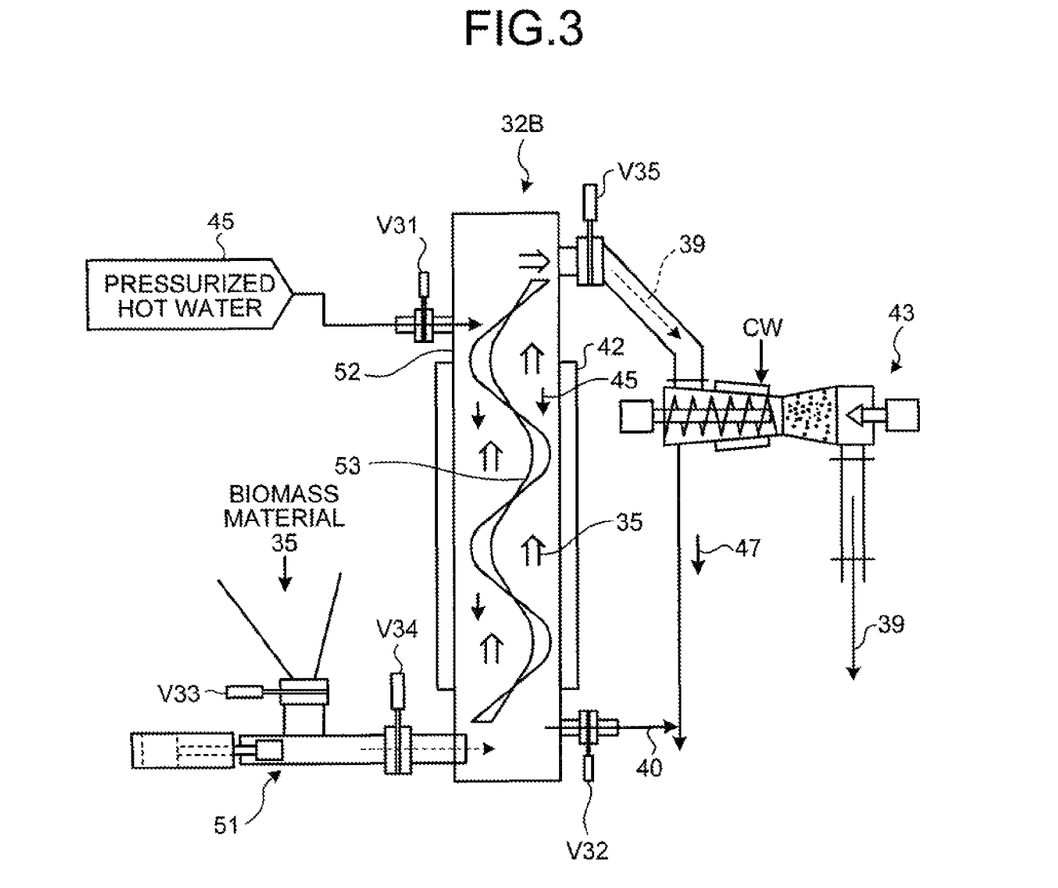
FIG. 3 is a conceptual diagram of another configuration of the hydrothermal decomposition device.

The configuration of the hydrothermal decomposition device 32A is not limited to that shown in FIG. 2. FIG. 3 is a conceptual diagram of another configuration of the hydrothermal decomposition device. As shown in FIG. 3, a biomass hydrothermal decomposition device 32B according to the present embodiment includes a biomass supply device 51, a reaction device 52, and the biomass discharge device 43. V31 to V35 denote differential pressure control valves (ON-OFF valves).

The biomass supply device 51 supplies the biomass material (such as wheat straw, in the present embodiment) 35 from under a normal pressure to under an increased pressure. Examples of the biomass supply device 51 include units such as a screw feeder, a piston pump, and a slurry pump.

The reaction device 52 gradually moves the supplied biomass material 35 from an upper or lower end side (a lower end side in the present embodiment) into a vertical device main body (hereinafter, "device main body") in a consolidated condition, and supplies the pressurized hot water 45 into the device main body from the end side (the upper end side in the present embodiment) different from the end side from which the biomass material 35 is supplied. In addition, the reaction device 52 hydrothermally decomposes the biomass material 35 while causing the biomass material 35 to countercurrently contact the pressurized hot water 45, transfers the lignin components and the hemicellulose components into the pressurized hot water 45, and separates the lignin components and the hemicellulose components from the biomass material 35.

As described above, the biomass discharge device 43 discharges the solid residual fraction 39 that is the biomass solid content from the supply side of the pressurized hot water 45 of the device main body.

A fixed agitating unit 53 that agitates the biomass material 35 in a so-called consolidated condition of a plug flow is provided within the device main body. By rotation of the fixed agitating unit 53, the biomass material 35 is agitated in response to an agitation action generated by the rotation of the fixed agitating unit 53 when the biomass material 35 fed into the device main body is moved in an axial direction. By providing the fixed agitating unit 53 within the device main body, mixing of the pressurized hot water 45 with a surface of the solid and an interior of the solid and the reaction is promoted in the device main body.

It is preferable that the flow of the pressurized hot water 45 and that of the biomass material 35 within the main body of the hydrothermal decomposition device 32B are the so-called counter flows for causing the biomass material 35 and the pressurized hot water 45 to countercurrently contact each other so that the biomass material 35 and the pressurized hot water 45 can contact each other, can be agitated, and can flow with views of efficiently mixing the biomass material 35 with the pressurized hot water 45 and promoting the reaction.

The hydrothermal decomposition device 32B hydrothermally decomposes the biomass material 35 by means of the plug flow. Therefore, the hydrothermal decomposition device 32B is simple in structure and the biomass material 35 that is solid is moved in parallel to a central axis of a pipe while being agitated perpendicularly to be central axis of the pipe. On the other hand, the pressurized hot water 45 (hot water, a liquid into which the decomposed material is dissolved) moves while soaking in the solid particles in the counter flow to the flow of the solid.

Furthermore, the plug flow can realize the uniform flow of the pressurized hot water 45. When the solid biomass material 35 is decomposed by the pressurized hot water 45, the decomposed material is dissolved into the hot water. The viscosity is high near decomposed portions, hot water moves preferentially to near non-decomposed portions, and the non-decomposed portions are decomposed subsequently to the decomposed portions. This can create the uniform flow of the hot water and uniform decomposition.

The hydrothermal decomposition device 32B includes the fixed agitating unit 53 within the device main body. Because of resistance of a pipe wall on an inside surface of the device main body of the hydrothermal decomposition device 32B, a solid concentration of the biomass material 35 on an outlet side decreases as compared with that of the biomass material 35 on an inlet side, and the solid residual fraction 39 that is the biomass solid content decrease by decomposition. Accordingly, a ratio of the pressurized hot water 45 increase, and the decomposed components in the liquid are excessively decomposed as a result of an increase in a liquid residence time. Therefore, by providing at least the fixed agitating unit 53 within the device main body, the hydrothermal decomposition device 32B can suppress the ratio of the pressurized hot water 45 and reduce the liquid residence time, thereby making it possible to suppress the decomposed components in the liquid from being excessively decomposed.

As shown in FIG. 1, in the saccharide-solution producing apparatus 11A according to the present embodiment, the solid residual fraction 39 and the hydrothermally discharged fraction 40 are discharged from the hydrothermal decomposition device 32A as the hydrothermally treated biomass. The solid residual fraction 39 in the hydrothermally treated biomass is supplied to the second enzymatic saccharification tank (C6) 33, and the hydrothermally discharged fraction 40 is supplied to the enzymatic saccharification tank (C5) 34.

The enzymatic saccharification tank (C6) 33 performs an enzymatic treatment on cellulose contained in the solid residual fraction 39 discharged from the hydrothermal decomposition device 32A with first enzyme (cellulase) 61, thereby obtaining a first saccharide solution 62 containing hexose.

The second enzymatic saccharification tank (C5) 34 performs an enzymatic treatment on the hemicellulose components transferred into the hydrothermally discharged fraction 40 discharged from the hydrothermal decomposition device 32A with second enzyme 63, thereby obtaining a second saccharide solution 64 containing pentose.

One of or both of the first saccharide solution 62 obtained in the enzymatic saccharification tank (C6) 33 and the second saccharide solution 64 obtained in the enzymatic saccharification tank (C5) 34 is used as the diluted saccharide solution 37. As described above, this diluted saccharide solution 37 is supplied to one of or both of the storage tank 25 and the first enzymatic saccharification tank 27 via a diluted-saccharide-solution supply pipe L11.

The diluted-saccharide-solution supply pipe L11 includes a diluted-saccharide-solution supply pipe L11-1 connected to the enzymatic saccharification tank (C6) 33, a diluted-saccharide-solution supply pipe L11-2 connected to the enzymatic saccharification tank (C5) 34, a diluted-saccharide-solution supply pipe L11-3 that supplies the diluted saccharide solution 37 to the saccharide-solution controlling unit 15A from a portion in which the diluted-saccharide-solution supply pipe L11-1 is connected to the diluted-saccharide-solution supply pipe L11-2, a diluted-saccharide-solution supply pipe L11-4 that connects the diluted-saccharide-solution supply pipe L11-3 to the storage tank 25, and a diluted-saccharide-solution supply pipe L11-5 that connects the diluted-saccharide-solution supply pipe L11-3 to the first enzymatic saccharification tank 27.

A control valve V11 is provided on the diluted-saccharide-solution supply pipe L11-1, a control valve V12 is provided on the diluted-saccharide-solution supply pipe L11-2, a control valve V21 is provided on the diluted-saccharide-solution supply pipe L11-4, and a control valve V22 is provided on the diluted-saccharide-solution supply pipe L11-5. The control valve V11 controls an amount of the first saccharide solution 62 discharged from the enzymatic saccharification tank (C6) 33, and the control valve V12 controls an amount of the second saccharide solution 64 discharged from the enzymatic saccharification tank (C5) 34. Furthermore, the control valve V21 controls the diluted saccharide solution 37 supplied to the storage tank 25, and the control valve V22 controls the diluted saccharide solution 37 supplied to the first enzymatic saccharification tank 27.

Therefore, the diluted saccharide solution 37 produced in the cellulosic biomass saccharifying unit 16 can be supplied to one of or both of the storage tank 25 and the first enzymatic saccharification tank 27 via the diluted-saccharide-solution supply pipe L11. That is, in a regulation stage before the carbohydrate-based material 21 is saccharified and the saccharide solution 22 is produced in the saccharide-solution controlling unit 15A, for example, in the present embodiment, a stage where carbohydrate-based material 21 is ground or pulverized by the grinding machine 23 and the pulverizer 24 and transferred to the storage tank 25 or a stage where the first enzymatic saccharification tank 27 performs saccharification (including a stage before the saccharification in a batch system), the diluted saccharide solution 37 produced by the cellulosic biomass saccharifying unit 16 is supplied. The saccharide concentration of the saccharide solution 22 obtained from the carbohydrate-based material 21 can be thereby set to a predetermined saccharide concentration (15 mass %, for example). Furthermore, by using the first saccharide solution 62 and the second saccharide solution 64 as the diluted solution used when saccharifying the carbohydrate-based material 21, the consumption of water for dilution can be suppressed. Therefore, it is possible to reduce the cost required to produce the saccharide solution 22.

Conventionally, when the carbohydrate-based material 21 is saccharified and the saccharide solution 22 is produced, half of components contained in the carbohydrate-based material 21 are starch and the saccharide concentration of the saccharide solution obtained when the carbohydrate-based material 21 is saccharified as it is 20% to 60%. When a high-concentration saccharide solution is used when producing alcohol, the saccharide-solution producing apparatus is put in a higher alcohol concentration condition as fermentation proceeds and microorganism become extinct. Therefore, it is impossible to use the high-concentration saccharide solution as it is. Therefore, it is necessary to dilute the carbohydrate-based material 21 with water and to produce the saccharide solution 22 when the carbohydrate-based material 21 is saccharified and the saccharide solution 22 is produced. On the other hand, when the biomass material 35 is saccharified and the saccharide solution 22 is produced, the concentration of the hydrothermally treated biomass (the solid residual fraction 39 and the hydrothermally discharged fraction 40) discharged from the biomass material 35 is low. Therefore, it is necessary to increase the concentration of the hydrothermally treated biomass (the solid residual fraction 39 and the hydrothermally discharged fraction 40) or to increase addition amounts of the first enzyme 61 and the second enzyme 63 by which these enzymes are added to the hydrothermally treated biomass (the solid residual fraction 39 and the hydrothermally discharged fraction 40), to increase saccharide concentrations of the obtained first saccharide solution 62 and the second saccharide solution 64, and to produce the saccharide solution 22.

On the other hand, according to the saccharide-solution producing apparatus 11A of the present embodiment, by using the first saccharide solution 62 and the second saccharide solution 64 as the diluted solution used when saccharifying the carbohydrate-based material 21, it is possible to reduce the saccharide concentration of the saccharide solution obtained from the carbohydrate-based material 21 and to produce the saccharide solution 22 at the predetermined saccharide concentration (15 mass %, for example) without increasing the saccharide concentration of the first saccharide solution 62 and the second saccharide solution 64. Furthermore, it is possible to suppress the consumption of the water used when saccharifying the carbohydrate-based material 21. It is thereby possible to obtain the saccharide solution 22 at the preferable concentration for alcohol fermentation or the like, and to reduce the cost required to produce the saccharide solution 22.

In the present embodiment, the first saccharide solution 62 and the second saccharide solution 64 obtained by saccharifying the solid residual fraction 39 and the hydrothermally discharged fraction 40 that are discharged from the hydrothermal decomposition device 32A are supplied, as the diluted saccharide solution 37, to one of or both of the storage tank 25 and the first enzymatic saccharification tank 27. However, the present invention is not limited thereto. Alternatively, either the first saccharide solution 62 or the second saccharide solution 64 can be supplied, as the diluted saccharide solution 37, to one of or both of the storage tank 25 and the first enzymatic saccharification tank 27.

After the saccharide solution 22 at the predetermined concentration is produced in the first enzymatic saccharification tank 27, the saccharide solution 22 that is an alcohol fermentation material is supplied to the alcohol fermentation tank 12 by way of a saccharide-solution supply line L12.

The alcohol fermentation tank 12 is a fermentation tank in which microorganism are added to the saccharide solution 22 to cause fermentation and in which alcohol (an organic material) is produced. The alcohol fermentation tank 12 performs a fermentation treatment by added microorganism 65 under predetermined conditions.

An alcohol fermentation liquid 71 obtained as a result of the alcohol fermentation is supplied to the distillation column 13 by way of a fermentation-liquid supply line L13 and distilled in the distillation column 13. Distillate 72 obtained as a result of distillation is passed through an alcohol supply line L14, purified by a refining device such as a dehydrator 73, supplied to the alcohol tank 14, and stored in the alcohol tank 14. Alcohol 74 such as ethanol that is a product is supplied from this alcohol tank 14 by way of a supply line L15 as needed.

A residue 75 in the alcohol fermentation tank 12 is discharged by way of a yeast-residue discharge line L21. Furthermore, a distillation residue 76 in the distillation column 13 is discharged by way of a distillation-residue discharge line L21, passed through a separator 77, a dryer 78, and a refrigerator 79, and discharged as distilled residue 800.

When the alcohol 74 is produced by the use of the alcohol producing system 10A, when a production volume of the alcohol 74 is 100000 kl/year, then that of the carbohydrate-based material 21 can be set to 90000 kl/year and that of the biomass material 35 can be set to 10000 kl/year. As compared with a case of producing the alcohol 74 using only the carbohydrate-based material 21, the alcohol 74 can be produced in the same amount as the conventional amount while suppressing the annual use of the carbohydrate-based material 21.

As described above, according to the alcohol producing system 10A that includes the saccharide-solution producing apparatus 11A of the present embodiment, the diluted saccharide solution 37 derived from the biomass material 35 produced in the cellulosic biomass saccharifying unit 16 is supplied to one of or both of the storage tank 25 and the first enzymatic saccharification tank 27 via the diluted-saccharide-solution supply line L11, and the diluted saccharide solution 37 is mixed in the regulation stage before producing the saccharide solution 22 from the carbohydrate-based material 21. It is thereby possible to improve production efficiency of the saccharide solution 22 obtained from the carbohydrate-based material 21, to set the saccharide concentration of the saccharide solution 22 to the predetermined saccharide concentration (15 mass %, for example), and to reduce the cost required to produce the saccharide solution 22. As a result, by producing the saccharide solution 22 at the predetermined saccharide concentration by the use of the diluted saccharide solution 37 derived from the biomass material 35 when the saccharide solution 22 derived from the carbohydrate-based material 21 is controled, it is possible to improve producing efficiency for producing the alcohol 74 and to reduce the cost required to produce the alcohol 74.

In the present embodiment, examples of the carbohydrate-based material 21 include cereal crops such as corn, rice, wheat, barley, and cassava. However, the present invention is not particularly limited thereto.

Figure 4:
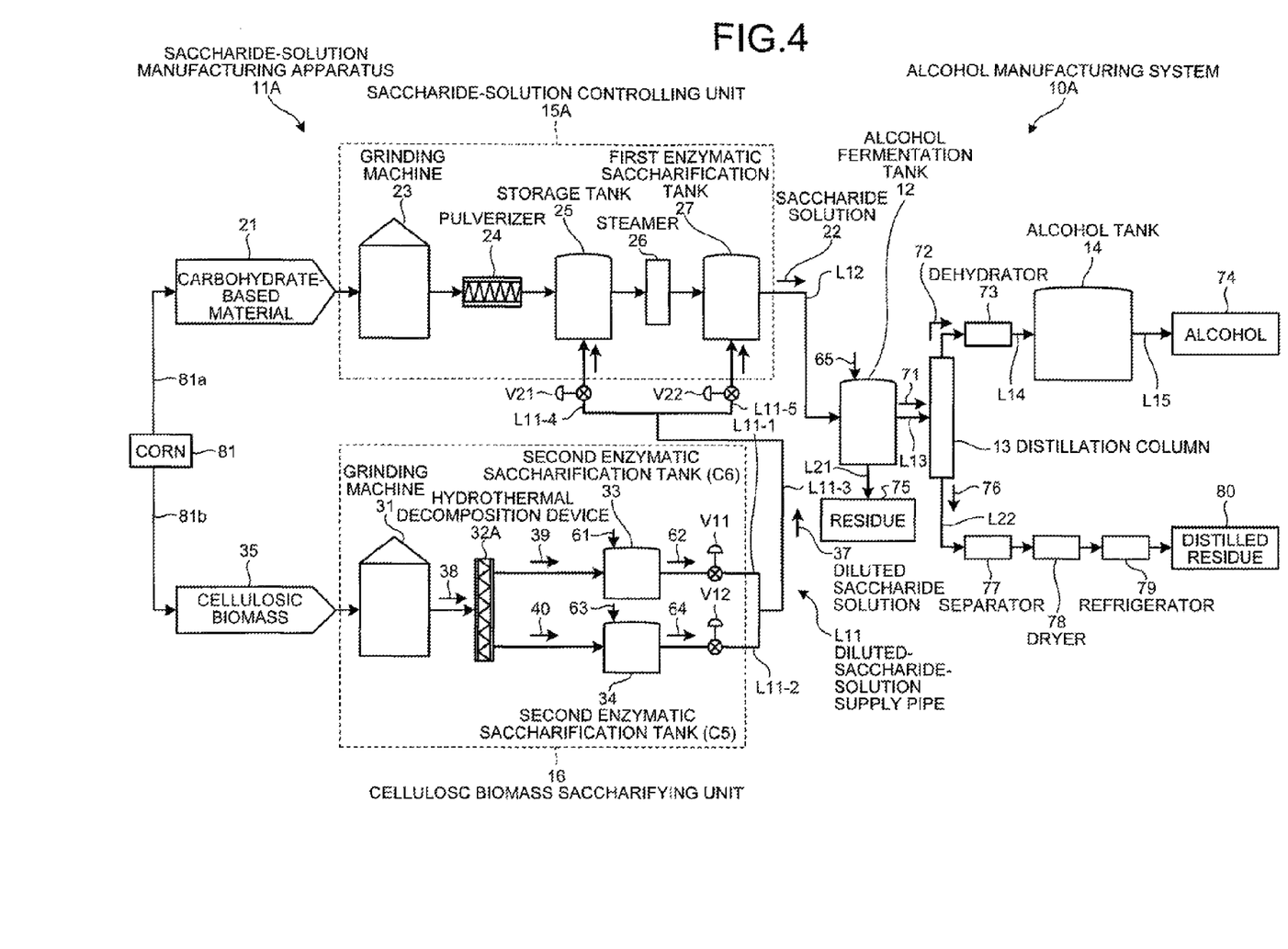
FIG. 4 is an example of a case where corns are applied as a material.

For example, when corns 81 are used as the carbohydrate-based material 21, both the carbohydrate-based material 21 such as kernels and the cellulosic biomass material 35 such as leaves, stalks and cobs of the corns are obtained from the corns 81. Therefore, it is possible to produce the saccharide solution 22 further efficiently. FIG. 4 is an example of a case where the corns 81 are applied as the material. As shown in FIG. 4, both the carbohydrate-based material 21 such as kernels 81a and the cellulosic biomass material 35 such as leaves, stalks and cobs of the corns 81b are obtained from the corns 81. Accordingly, the kernels 81a and the like can be used as the carbohydrate-based material 21, and the leaves, stalks, and cobs of the corns 81b can be used as the cellulosic biomass material 35. According to the saccharide-solution producing apparatus 11A of the present embodiment, it is possible to obtain the saccharide solution 22 further efficiently and to improve efficiency of producing an organic material such as the alcohol 74 without generating waste from one material such as the corns 81.

In the present embodiment, the case of fermenting alcohol that is the organic material by the use of the saccharide solution 22 has been described as the fermentation system. However, the fermentation system using the saccharide solution according to the present embodiment is not limited to this system. While it has been described by way of example that the alcohol (ethanol, methanol or the like) that is the organic material is obtained by the fermentation treatment, the present invention is not limited to these examples. Alternatively, a petroleum substitute that is a chemical-product material or amino acid that is a food or feedstuff material other than the alcohol can be obtained by the fermentation apparatus.

Examples of chemical products obtained from the saccharide solution 22 include LPG, automobile fuel, aircraft jet fuel, heating oil, diesel oil, various types of heavy oil, fuel gas, naphtha, ethylene glycol that is a naphtha decomposed material, ethanol, amine, lactic acid, alcohol ethoxylate, vinyl chloride polymer, aluminum alkyl, PVA, acetic acid vinyl emulsion, polystyrene, polyethylene, polypropylene, polycarbonate, MMA resin, nylon, and polyester. Therefore, the diluted saccharide solution 37 derived from biomass can be efficiently used as substitutes for chemical products derived from crude oil that is exhaustible fuel and materials for producing the substitutes.

Second Embodiment

Figure 5:
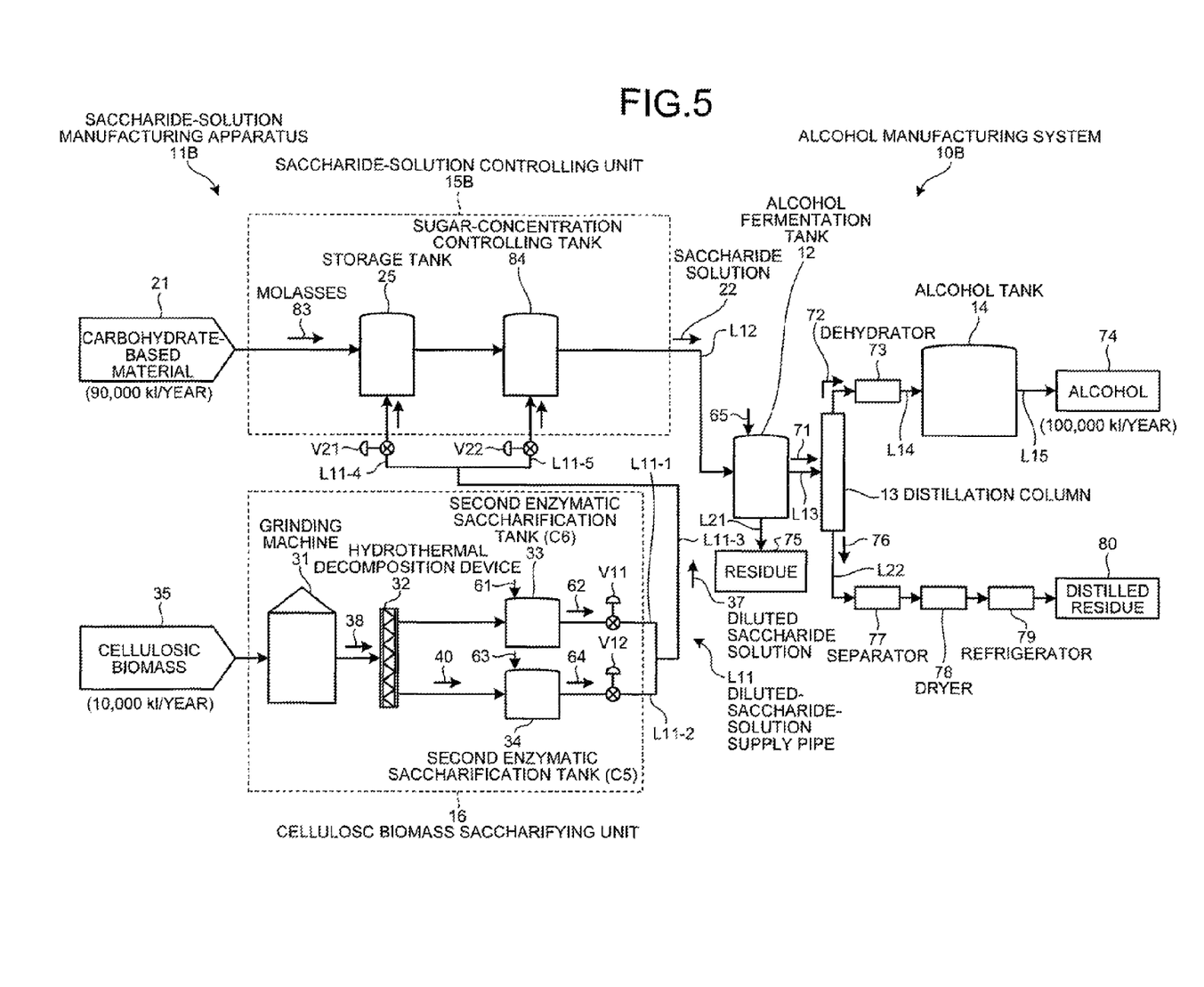
FIG. 5 is a schematic diagram of an alcohol producing system including a saccharide-solution producing apparatus according to a second embodiment of the present invention.

A saccharide-solution producing apparatus according to a second embodiment of the present invention is described with reference to the drawings. FIG. 5 is a schematic diagram of an alcohol producing system including the saccharide-solution producing apparatus according to the second embodiment of the present invention. Because the configuration of the saccharide-solution producing apparatus according to the present embodiment is identical to that of the alcohol producing system including the saccharide-solution producing apparatus according to the first embodiment of the present invention shown in FIG. 1, members identical to those according to the first embodiment are denoted by like reference signs and redundant explanations thereof will be omitted.

As shown in FIG. 5, an alcohol producing system 10B includes a saccharide-solution producing apparatus 11B according to the present embodiment, the alcohol fermentation tank 12, the distillation column 13, and the alcohol tank 14.

The saccharide-solution producing apparatus 11B according to the present embodiment uses molasses 83 as a saccharification material obtained from the carbohydrate-based material 21 of the saccharide-solution producing apparatus 11A according to the first embodiment of the present invention shown in FIG. 1. That is, the saccharide-solution producing apparatus 11B according to the present embodiment includes a saccharide-solution controlling unit 15B and the cellulosic biomass saccharifying unit 16.

The saccharide-solution controlling unit 15B produces the saccharide solution 22 from the molasses 83. The saccharide-solution controlling unit 15B includes the storage tank 25 and a saccharide-concentration controlling tank 84. The molasses 83 is discharged or squeezed from the carbohydrate-based material 21. The molasses 83 obtained from the carbohydrate-based material 21 is stored in the storage tank 25. A saccharide concentration of the molasses 83 stored in the storage tank 25 is controled by the saccharide-concentration controlling tank 84.

Because the cellulosic biomass saccharifying unit 16 is identical to that in the saccharide-solution producing apparatus 11 according to the first embodiment of the present invention described above, explanations thereof will be omitted.

The diluted saccharide solution 37 produced in the cellulosic biomass saccharifying unit 16 is supplied to one of or both of the storage tank 25 and the saccharide-concentration controlling tank 84 via the diluted-saccharide-solution supply pipe L11. It is thereby possible to mix the diluted saccharide solution 37 with the molasses 83 obtained from the carbohydrate-based material 21. That is, in the saccharide-solution controlling unit 15B, in the regulation stage before producing the saccharide solution 22 from the molasses 83 obtained from the carbohydrate-based material 21, the diluted saccharide solution 37 produced in the cellulosic biomass saccharifying unit 16 is supplied to the molasses 83.\

The saccharide concentration of the molasses 83 obtained from the carbohydrate-based material 21 can be set to a predetermined saccharide concentration (15 mass %, for example). Furthermore, by using the first saccharide solution 62 and the second saccharide solution 64 as the diluted solution used when saccharifying the carbohydrate-based material 21, the consumption of water for dilution can be suppressed. Therefore, it is possible to reduce the cost required to produce the saccharide solution 22.

Thus, according to the saccharide-solution producing apparatus 11B of the present embodiment, by using the first saccharide solution 62 and the second saccharide solution 64 as the diluted solution used when saccharifying the carbohydrate-based material 21, it is possible to reduce the saccharide concentration of the molasses 83 obtained from the carbohydrate-based material 21 and to produce the saccharide solution 22 at the predetermined saccharide concentration (15 mass %, for example) without increasing the saccharide concentration of the first saccharide solution 62 and the second saccharide solution 64. Furthermore, it is possible to suppress the consumption of the water used when producing the saccharide solution 22 from the molasses 83. It is thereby possible to obtain the saccharide solution 22 at the preferable concentration for alcohol fermentation or the like, and to reduce the cost required to produce the saccharide solution 22.

Therefore, according to the alcohol producing system 10B that includes the saccharide-solution producing apparatus 11B of the present embodiment, the saccharide solution 22 at the predetermined saccharide concentration is produced using the diluted saccharide solution 37 derived from the biomass material 35 when the molasses 83 derived from the carbohydrate-based material 21 is controlled. It is thereby possible to improve the producing efficiency for producing the alcohol 74 and to reduce the cost required to produce the alcohol 74.

In the present embodiment, while the case of using molasses as the saccharification material obtained from the carbohydrate-based material 21 has been explained, the present invention is not limited thereto. It suffices that the saccharification material is a material such as sugarcane or sugar beet that is obtained by being discharged or squeezed from the carbohydrate-based material 21.

Figure 6:
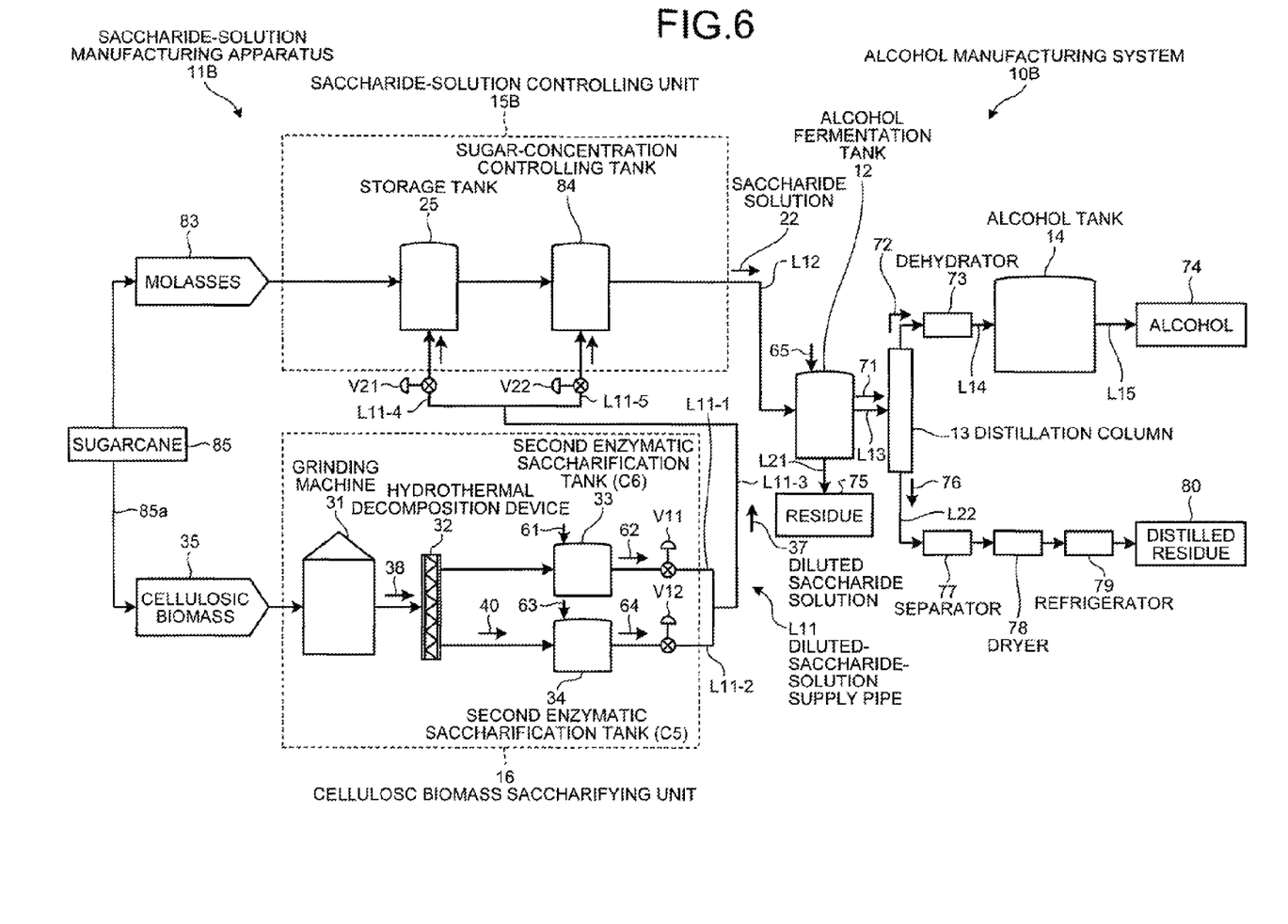
FIG. 6 is an example of a case where sugarcane is applied as a material.

For example, when sugarcane is used as the material, molasses is obtained as the carbohydrate-based material 21 from the sugarcane, and the cellulosic biomass material 35 such as a residue (bagasse) obtained when squeezing saccharides from leaves or the sugarcane is obtained. Therefore, it is possible to produce the saccharide solution 22 further efficiently. FIG. 6 is an example of a case where sugarcane is applied as the material. As shown in FIG. 6, both the molasses 83 that is the carbohydrate-based material 21 and the cellulosic biomass material 35 such as leaves and bagasse 85B are obtained from sugarcane 85. As a result, the molasses 83 can be used as the carbohydrate-based material 21, and the leaves, the bagasse 85B and the like can be used as the cellulosic biomass material 35. Therefore, according to the saccharide-solution producing apparatus 11B of the present embodiment, it is possible to obtain the saccharide solution 22 further efficiently and to improve the efficiency of producing the organic material such as the alcohol 74 without generating waste from one material.

REFERENCE SIGNS LIST 10A, 10B alcohol producing system
11A, 11B saccharide-solution producing apparatus
12 alcohol fermentation tank
13 distillation column
14 alcohol tank
15A, 15B saccharide-solution controlling unit
16 cellulosic biomass saccharifying unit
21 carbohydrate-based material
22 saccharide solution
23, 31 grinding machine
24 pulverizer
25 storage tank
26 cooker
27 first enzymatic saccharification tank
32A, 32B hydrothermal decomposition device
33 second enzymatic saccharification tank (C6)
34 second enzymatic saccharification tank (C5)
35 cellulosic biomass material (biomass material)
37 diluted saccharide solution
38 ground biomass material
39 solid residual fraction
40 hydrothermally treated fraction
41, 51 biomass supply device
42, 52 reaction device
43 biomass discharge device
44 screw unit
45 pressurized hot water
47 dehydration liquid
48 pressurized nitrogen ($N_2$)
49 temperature jacket
53 fixed agitating unit
61 first enzyme (cellulase)
62 first saccharide solution
63 second enzyme
64 second saccharide solution
65 microbe
71 alcohol fermentation liquid
72 distillate
73 dehydrator
74 alcohol
75 residue
76 distillation residue
77 separator
78 dryer
79 refrigerator
80 distilled residue
81 corn
83 molasses
84 saccharide-concentration controlling tank
85 sugarcane
L11, L11-1 to L11-5 diluted-saccharide-solution supply pipe
V11, V12, V21, V22 control valve
V31 to V35 differential pressure control valve (ON-OFF valve)

The invention claimed is:
1. A saccharide-solution producing apparatus comprising:
a saccharide-solution controlling unit including:
a storage tank that stores a carbohydrate-based material containing starch as a main component; and
a first enzymatic saccharification tank that saccharifies the carbohydrate-based material so as to produce a saccharide solution,
a cellulosic biomass saccharifying unit including:
a hydrothermal decomposition device that hydrothermally decomposes a cellulosic biomass material containing a lignin component and a hemicellulose component so as to produce hydrothermally treated biomass; and
a second enzymatic saccharification tank that saccharifies the hydrothermally treated biomass so as to produce a diluted saccharide solution having a concentration equal to or higher than 0.1 mass % and equal to or lower than 15 mass %; and a diluted-saccharide-solution supply pipe that connects the second enzymatic saccharification tank to the storage tank and the first enzymatic saccharification tank so as to supply the diluted saccharide solution to the storage tank and the first enzymatic saccharification tank.

2. The saccharide-solution producing apparatus according to claim 1, wherein
the hydrothermal decomposition device hydrothermally decomposes the cellulosic biomass material while causing the cellulosic biomass material to contact pressurized hot water, transfers a lignin component and a hemicellulose component into the pressurized hot water, and separates the lignin component and the hemicellulose component from the cellulosic biomass material, and
a hydrothermally discharged fraction that contains the lignin component and the hemicellulose component and a solid residual fraction that contains a cellulose component are produced as the hydrothermally treated biomass.

3. The saccharide-solution producing apparatus according to claim 2, wherein
the second enzymatic saccharification tank includes a first diluted saccharide solution producing enzymatic saccharification tank that produces as the diluted-saccharide-solution a first diluted saccharide solution that contains hexose by adding enzyme to the solid residual fraction discharged from the hydrothermal decomposition device and enzymatically decomposing a cellulose component contained in the solid residual fraction, and a second diluted saccharide solution producing enzymatic saccharification tank that produces as the diluted-saccharide-solution a second diluted saccharide solution that contains pentose by adding enzyme to the hydrothermally discharged fraction discharged from the hydrothermal decomposition device and enzymatically decomposing a hemicellulose component contained in the hydrothermally discharged fraction, wherein
one of or both of the first diluted saccharide solution and the second diluted saccharide solution are produced, and
the diluted-saccharide-solution supply pipe is connected to the first diluted saccharide solution producing enzymatic saccharification tank that produces the first diluted saccharide solution and the second diluted saccharide solution producing enzymatic saccharification tank that produces the second diluted saccharide solution so that at least one of the first diluted saccharide solution and the second diluted saccharide solution can be supplied.

4. A fermentation system comprising:
the saccharide-solution producing apparatus according to claim 1; and
an alcohol fermentation tank that ferments the saccharide solution to produce an organic material.

5. A saccharide-solution producing apparatus comprising:
a saccharide-solution controlling unit including:
a storage tank that stores molasses obtained from carbohydrate-based material by discharging or squeezing from the carbohydrate-based material; and
a sugar-concentration controlling tank that controls a saccharide concentration of the molasses,
a cellulosic biomass saccharifying unit including:
a hydrothermal decomposition device that hydrothermally decomposes a cellulosic biomass material containing a lignin component and a hemicellulose component so as to produce hydrothermally treated biomass; and
an enzymatic saccharification tank that saccharifies the hydrothermally treated biomass so as to produce a diluted saccharide solution having a concentration equal to or higher than 0.1 mass % and equal to or lower than 15 mass %; and
a diluted-saccharide-solution supply pipe that connects the enzymatic saccharification tank to the storage tank and the sugar-concentration controlling tank so as to supply the diluted saccharide solution to the storage tank and the sugar-concentration controlling tank.

6. The saccharide-solution producing apparatus according to claim 5, wherein
the hydrothermal decomposition device hydrothermally decomposes the cellulosic biomass material while causing the cellulosic biomass material to contact pressurized hot water, transfers a lignin component and a hemicellulose component into the pressurized hot water, and separates the lignin component and the hemicelluloses component from the cellulosic biomass material, and
a hydrothermally discharged fraction that contains the lignin component and the hemicellulose component and a solid residual fraction that contains a cellulose component are produced as the hydrothermally treated biomass.

7. The saccharide-solution producing apparatus according to claim 6, wherein
the second enzymatic saccharification tank includes a first diluted saccharide solution producing enzymatic saccharification tank that produces as the diluted-saccharide-solution a first diluted saccharide solution that contains hexose by adding enzyme to the solid residual fraction discharged from the hydrothermal decomposition device and enzymatically decomposing a cellulose component contained in the solid residual fraction, and a second diluted saccharide solution producing enzymatic saccharification tank that produces as the diluted-saccharide-solution a second diluted saccharide solution that contains pentose by adding enzyme to the hydrothermally discharged fraction discharged from the hydrothermal decomposition device and enzymatically decomposing a hemicellulose component contained in the hydrothermally discharged fraction, wherein
one of or both of the first diluted saccharide solution and the second diluted saccharide solution are produced, and
the diluted-saccharide-solution supply pipe is connected to the first diluted saccharide solution producing enzymatic saccharification tank that produces the first diluted saccharide solution and the second diluted saccharide solution producing enzymatic saccharification tank that produces the second diluted saccharide solution so that at least one of the first diluted saccharide solution and the second diluted saccharide solution can be supplied.

8. A fermentation system comprising:
the saccharide-solution producing apparatus according to claim 5; and
an alcohol fermentation tank that ferments the saccharide solution to produce an organic material.

9. The saccharide solution producing apparatus according to claim 1, further comprising a control valve provided on the diluted-saccharide solution supply pipe that controls an amount of the diluted saccharide solution supplied to the storage tank and the first enzymatic saccharification tank.

10. The saccharide solution producing apparatus according to claim 5, further comprising a control valve provided on the diluted-saccharide solution supply pipe that controls an amount of the diluted saccharide solution supplied to the storage tank and the sugar-concentration controlling tank.

* * * * *